(12) United States Patent
Chakrabarty et al.

(10) Patent No.: US 8,949,038 B2
(45) Date of Patent: Feb. 3, 2015

(54) CONTROLLING BITUMEN QUALITY IN SOLVENT-ASSISTED BITUMEN EXTRACTION

(75) Inventors: Tapantosh Chakrabarty, Calgary (CA); Ken N. Sury, Calgary (CA); Joseph L. Feimer, Bright's Grove (CA)

(73) Assignee: ExxonMobil Upstream Research Company, Houston, TX (US)

( * ) Notice: Subject to any disclaimer, the term of this patent is extended or adjusted under 35 U.S.C. 154(b) by 106 days.

(21) Appl. No.: 13/813,028

(22) PCT Filed: Jun. 23, 2011

(86) PCT No.: PCT/US2011/041631
§ 371 (c)(1),
(2), (4) Date: Jan. 29, 2013

(87) PCT Pub. No.: WO2012/039804
PCT Pub. Date: Mar. 29, 2012

(65) Prior Publication Data
US 2013/0168294 A1 Jul. 4, 2013

(30) Foreign Application Priority Data
Sep. 22, 2010 (CA) ..................... 2714842

(51) Int. Cl.
*C10G 1/00* (2006.01)
*C10G 1/04* (2006.01)
(Continued)

(52) U.S. Cl.
CPC *C10G 1/008* (2013.01); *C10G 1/04* (2013.01); *C10G 21/003* (2013.01);
(Continued)

(58) Field of Classification Search
USPC .............. 208/390; 73/53.01; 436/91, 96, 123; 702/22, 25, 32
See application file for complete search history.

(56) References Cited

U.S. PATENT DOCUMENTS 4,057,486 A 11/1977 Meadus et al.
4,676,889 A 6/1987 Hsieh et al.
(Continued)

FOREIGN PATENT DOCUMENTS

CA 940853 1/1974
CA 2068895 5/1993
(Continued)

OTHER PUBLICATIONS

Sparks, B. D. et al. (1992) "The Effect of Asphaltene Content on Solvent Selection for Bitumen Extraction by the SESA Process," *Fuel*, (71); pp. 1349-1353.
(Continued)

*Primary Examiner* — Brian McCaig
(74) *Attorney, Agent, or Firm* — ExxonMobil Upstream Research-Law Department (57) ABSTRACT

Described herein is a method of controlling bitumen quality in a process stream within a solvent-assisted bitumen extraction operation, for instance a hydrocarbon stream from a froth separation unit (FSU). Bitumen quality is a measure of the amount of selected contaminants in the process stream. Contaminants may include asphaltenes (comprising metal porphyrins), sulfur, and inorganic solids (comprising inorganic elements, e.g. Si, Al, Ti, Fe, Na, K, Mg, and Ca). First, the amounts of selected contaminants are measured. Next, these measured values are compared to maximum reference values. If one or more of these contaminants is higher than the maximum reference value, at least one variable of the solvent-assisted bitumen extraction is adjusted to improve bitumen quality.

19 Claims, 5 Drawing Sheets

(51) Int. Cl.
  *C10G 21/00*   (2006.01)
  *G01N 23/223*  (2006.01)
  *G01N 33/42*   (2006.01)
  *G01N 21/31*   (2006.01)

(52) U.S. Cl.
  CPC ......... *G01N 21/3103* (2013.01); *G01N 23/223* (2013.01); *G01N 33/42* (2013.01); *C10G 2300/202* (2013.01); *C10G 2300/206* (2013.01); *C10G 2300/44* (2013.01); *G01N 2223/076* (2013.01)
  USPC ............... 702/25; 702/23; 702/32; 73/53.01; 436/91; 436/96; 436/123

(56) References Cited

U.S. PATENT DOCUMENTS

| | | |
|---|---|---|
| 5,236,577 A | 8/1993 | Tipman et al. |
| 5,274,572 A | 12/1993 | O'Neill et al. |
| 5,781,430 A | 7/1998 | Tsai |
| 5,876,592 A | 3/1999 | Tipman et al. |
| 5,913,022 A | 6/1999 | Tinaztepe et al. |
| 5,920,718 A | 7/1999 | Uczekaj et al. |
| 5,968,349 A | 10/1999 | Duyvesteyn et al. |
| 6,007,709 A | 12/1999 | Duyvesteyn et al. |
| 6,028,819 A | 2/2000 | Mullarkey et al. |
| 6,074,558 A | 6/2000 | Duyvesteyn et al. |
| 6,182,014 B1 | 1/2001 | Kenyon et al. |
| 6,191,787 B1 | 2/2001 | Lu et al. |
| 6,195,092 B1 | 2/2001 | Dhond et al. |
| 6,214,213 B1 | 4/2001 | Tipman et al. |
| 6,323,679 B1 | 11/2001 | Robertson et al. |
| 6,358,403 B1 | 3/2002 | Brown et al. |
| 6,358,404 B1 | 3/2002 | Brown et al. |
| 6,374,252 B1 | 4/2002 | Althoff et al. |
| 6,401,081 B1 | 6/2002 | Montgomery et al. |
| 6,411,922 B1 | 6/2002 | Clark et al. |
| 6,498,988 B1 | 12/2002 | Robert et al. |
| 6,678,642 B1 | 1/2004 | Budge |
| 6,712,215 B2 | 3/2004 | Scheybeler |
| 6,731,994 B2 | 5/2004 | Heching et al. |
| 6,731,998 B2 | 5/2004 | Walser et al. |
| 6,800,116 B2 | 10/2004 | Stevens et al. |
| 6,829,570 B1 | 12/2004 | Thambynayagam et al. |
| 6,910,001 B2 | 6/2005 | Hammersley et al. |
| 6,934,931 B2 | 8/2005 | Plummer et al. |
| 6,980,935 B2 | 12/2005 | Lu et al. |
| 6,980,940 B1 | 12/2005 | Gurpinar et al. |
| 6,996,803 B2 | 2/2006 | Sakamoto et al. |
| 7,067,811 B2 | 6/2006 | Long et al. |
| 7,141,162 B2 | 11/2006 | Garner et al. |
| 7,296,274 B2 | 11/2007 | Cohen et al. |
| 7,376,472 B2 | 5/2008 | Wojsznis et al. |
| 7,451,066 B2 | 11/2008 | Edwards et al. |
| 7,478,024 B2 | 1/2009 | Gurpinar et al. |
| 7,499,841 B2 | 3/2009 | Hoffman |
| 7,516,446 B2 | 4/2009 | Choi et al. |
| 7,546,578 B2 | 6/2009 | Yang |
| 8,449,764 B2 * | 5/2013 | Chakrabarty et al. ......... 208/337 |
| 2003/0018490 A1 | 1/2003 | Magers et al. |
| 2003/0125818 A1 | 7/2003 | Johnson |
| 2003/0139907 A1 | 7/2003 | McCarthy |
| 2004/0054564 A1 | 3/2004 | Fonseca et al. |
| 2004/0111428 A1 | 6/2004 | Rajan et al. |
| 2005/0027559 A1 | 2/2005 | Rajan et al. |
| 2005/0150844 A1 | 7/2005 | Hyndman et al. |
| 2005/0188606 A1 | 9/2005 | Caprotti et al. |
| 2005/0263437 A1 | 12/2005 | Howdeshell |
| 2006/0111903 A1 | 5/2006 | Kemmochi et al. |
| 2006/0113218 A1 | 6/2006 | Hart et al. |
| 2006/0138036 A1 | 6/2006 | Garner et al. |
| 2006/0138055 A1 | 6/2006 | Garner et al. |
| 2006/0196812 A1 | 9/2006 | Beetge et al. |
| 2006/0249439 A1 | 11/2006 | Garner et al. |
| 2006/0260980 A1 | 11/2006 | Yeung |
| 2006/0282243 A1 | 12/2006 | Childs et al. |
| 2007/0111903 A1 | 5/2007 | Engel et al. |
| 2007/0156377 A1 | 7/2007 | Gurpinar et al. |
| 2007/0168057 A1 | 7/2007 | Blevins et al. |
| 2007/0168741 A1 | 7/2007 | Chadha et al. |
| 2008/0208552 A1 | 8/2008 | Kumar et al. |
| 2008/0288226 A1 | 11/2008 | Gurpinar et al. |

FOREIGN PATENT DOCUMENTS

| | | |
|---|---|---|
| CA | 2075108 | 1/1994 |
| CA | 2200899 | 9/1998 |
| CA | 2232929 | 9/1998 |
| CA | 2353109 | 1/2003 |
| CA | 2471048 | 3/2004 |
| CA | 2527058 | 3/2004 |
| CA | 2502943 | 5/2004 |
| CA | 2505411 | 7/2004 |
| CA | 2425840 | 10/2004 |
| CA | 2435113 | 1/2005 |
| CA | 2493677 | 6/2005 |
| CA | 2454942 | 7/2005 |
| CA | 2455011 | 7/2005 |
| CA | 2726122 | 7/2005 |
| CA | 2750837 | 7/2005 |
| CA | 2750845 | 7/2005 |
| CA | 2750934 | 7/2005 |
| CA | 2750936 | 7/2005 |
| CA | 2750939 | 7/2005 |
| CA | 2750995 | 7/2005 |
| CA | 2751587 | 7/2005 |
| CA | 2751773 | 7/2005 |
| CA | 2799354 | 7/2005 |
| CA | 2799400 | 7/2005 |
| CA | 2799739 | 7/2005 |
| CA | 2490734 | 6/2006 |
| CA | 2502329 | 9/2006 |
| CA | 2538464 | 9/2006 |
| CA | 2521248 | 3/2007 |
| CA | 2612791 | 5/2008 |
| CA | 2651155 | 8/2009 |
| CA | 2587166 | 5/2010 |
| CA | 2644821 | 5/2010 |
| CA | 2714735 | 7/2011 |
| CA | 2729457 | 7/2011 |
| CA | 2733862 | 7/2011 |
| CA | 2806588 | 7/2011 |
| CA | 2806891 | 7/2011 |
| CA | 2719874 | 5/2012 |
| CA | 2733332 | 8/2012 |
| CA | 2735311 | 9/2012 |
| CA | 2736082 | 9/2012 |
| CA | 2737410 | 10/2012 |
| CA | 2738700 | 10/2012 |
| CA | 2805804 | 10/2012 |
| CA | 2815785 | 10/2012 |
| CA | 2739667 | 11/2012 |
| CA | 2740823 | 11/2012 |
| CA | 2740935 | 11/2012 |
| WO | WO 99/33936 | 7/1999 |

OTHER PUBLICATIONS

ASTM D4807 (2010).

* cited by examiner

CONTROLLING BITUMEN QUALITY IN SOLVENT-ASSISTED BITUMEN EXTRACTION

CROSS-REFERENCE TO RELATED APPLICATIONS

This application is the National Stage of Internationl Application No. PCT/US2011/041631, filed Jun. 23, 2011, which claims priority from Canadian patent application number 2,714,842 filed on Sep. 22, 2010 entitled Controlling Bitumen Quality in Solvent-Assisted Bitumen Extraction, the entirety of which is incorporated by reference herein.

FIELD OF THE INVENTION

The present invention is in the field of hydrocarbon extraction from mineable deposits, such as bitumen from oil sands. More specifically, it relates to controlling bitumen quality in solvent-assisted bitumen extraction.

BACKGROUND OF THE INVENTION

Oil sand extraction processes are used to liberate and separate bitumen from oil sands so that the bitumen can be further processed to produce synthetic crude oil. Numerous oil sand extraction processes have been developed and commercialized, many of which involve the use of water as a processing medium. Other processes are non-aqueous solvent-based processes. Solvent may be used in both aqueous and non-aqueous processes.

One water-based extraction process is the Clark hot water extraction process (the "Clark Process"). This process typically requires that mined oil sands be conditioned for extraction by being crushed to a desired lump size and then combined with hot (for instance about 95° C.) water and perhaps other agents to form a conditioned slurry of water and crushed oil sands. In the Clark Process, an amount of sodium hydroxide (caustic) may be added to the slurry to adjust the slurry pH upwards, which enhances the liberation and separation of bitumen from the oil sands. Other water-based extraction processes may use other temperatures and may include other conditioning agents, which are added to the oil sand slurry, or may operate without conditioning agents.

Regardless of the type of water-based extraction process employed, the process will typically result in the production of a bitumen froth that requires treatment with a solvent. For example, in the Clark Process, a bitumen froth stream comprises bitumen, fine particulate solids (also referred to as mineral or inorganic solids) and water. Certain processes use naphtha to dilute bitumen froth before separating the product bitumen by centrifugation. These processes are called naphtha froth treatment (NFT) processes. Other processes use a paraffinic solvent, and are called paraffinic froth treatment (PFT) processes, to produce pipelineable bitumen with low levels of solids and water. In the PFT process, a paraffinic solvent (for example, a mixture of iso-pentane and n-pentane) is used to dilute the froth before separating the product, diluted bitumen, by gravity. A portion of the asphaltenes in the bitumen is also rejected by design in the PFT process and this rejection is used to achieve reduced solids and water levels. In both the NFT and the PFT processes, the diluted tailings—comprising water, solids and some hydrocarbon—are separated from the diluted product bitumen.

Solvent is typically recovered from the diluted product bitumen component before the bitumen is delivered to a refining facility for further processing.

One PFT process will now be described further, although variations of the process exist. The PFT process may comprise at least three units: Froth Separation Unit (FSU), Solvent Recovery Unit (SRU) and Tailings Solvent Recovery Unit (TSRU). Two FSUs may be used, as shown in FIG. 1.

Figure 1:
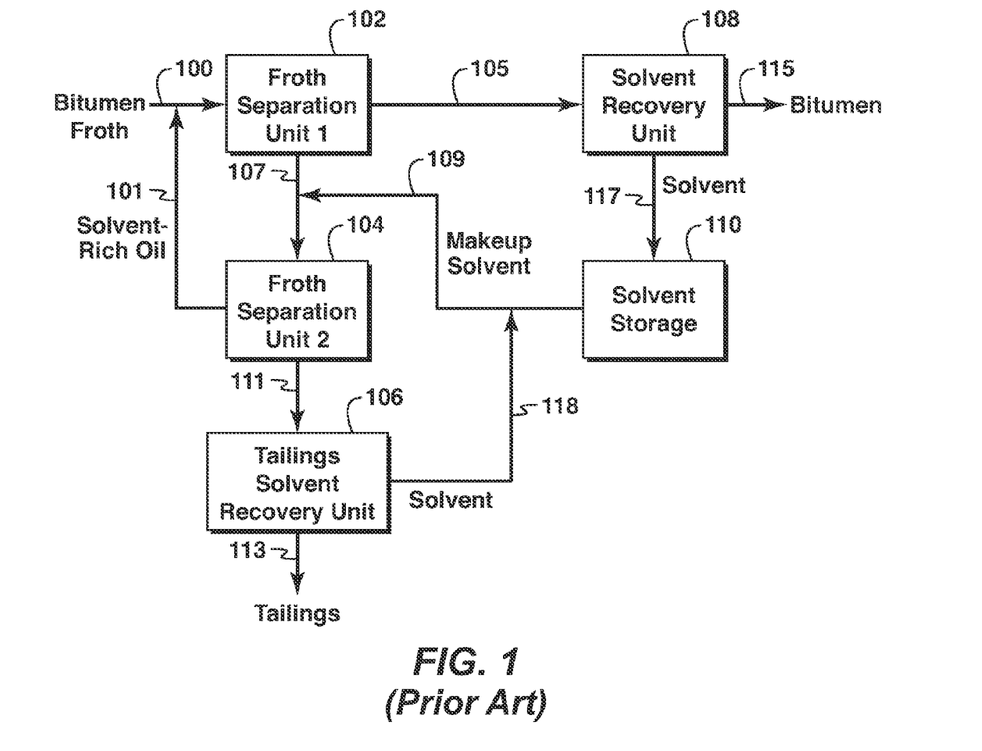
FIG. 1 is a flow diagram of a prior art paraffinic froth treatment process.

With reference to FIG. 1, mixing of solvent with the feed bitumen froth (100) is carried out counter-currently in two stages: FSU-1 and FSU-2, labeled as Froth Separation Unit 1 (102) and Froth Separation Unit 2 (104). The bitumen froth comprises bitumen, water, and fine solids (also referred to as mineral solids). A typical composition of bitumen froth is about 60 wt % bitumen, 30 wt % water, and 10 wt % solids. The paraffinic solvent is used to dilute the froth before separating the product bitumen by gravity. Examples of paraffinic solvents are pentane or hexane, either used alone or mixed with isomers of pentanes or hexanes, respectively. An example of a paraffinic solvent is a mixture of iso-pentane and n-pentane. In FSU-1 (102), the froth (100) is mixed with the solvent-rich oil stream (101) from the second stage (FSU-2) (104). The temperature of FSU-1 (102) is maintained at, for instance, about 60° C. to about 80° C., or about 70° C., while the solvent to bitumen (SB) ratio may be from 1.4:1 to 2.2:1 by weight or may be controlled around 1.6:1 by weight for a 60:40 mixture of n-pentane: iso-pentane. The overhead from FSU-1 (102) is the diluted bitumen product (105) (also referred to as the hydrocarbon leg) and the bottom stream from FSU-1 (102) is the tailings (107) comprising water, solids (inorganics), asphaltenes, and some residual bitumen. The residual bitumen from this bottom stream is further extracted in FSU-2 (104) by contacting it with fresh solvent (109), for instance, in a 25 to 30:1 (w/w) SB ratio at, for instance, about 80° C. to about 100° C., or about 90° C. Examples of operating pressures of FSU-1 and FSU-2 are about 550 kPag and 600 kPag, respectively. The solvent-rich oil (overhead) (101) from FSU-2 (104) is mixed with the fresh froth feed (100) as mentioned above. The bottom stream from FSU-2 (104) is the tailings (111) comprising solids, water, asphaltenes and residual solvent, which is to be recovered in the Tailings Solvent Recovery Unit (TSRU) (106) prior to the disposal of the tailings (113) in tailings ponds. The recovered solvent (118) from TSRU (106) is directed to the solvent storage (110). Solvent from the diluted bitumen overhead stream (105) is recovered in the Solvent Recovery Unit (SRU) (108) and passed as solvent (117) to Solvent Storage (110). Bitumen (115) exiting the SRU (108) is also illustrated. The foregoing in only an example of a PFT process and the values are provided by way of example only. An example of a PFT process is described in Canadian Patent No. 2,587,166 to Sury.

To meet bitumen product quality, it is important for the diluted bitumen from FSU-1 to be below a set maximum amount of contaminants. Bitumen quality refers to the amount of selected contaminants in the process stream. Contaminants may include asphaltenes (comprising metal porphyrins) and inorganic solids (comprising inorganic elements, e.g. Si, Al, Ti, Fe, Na, K, Mg, and Ca). Achieving target bitumen quality is important as the contaminants may adversely affect the refinery processing of the product bitumen.

One known method of determining the solids content is to analyze samples in a laboratory using ASTM D4807. This method is not suitable for controlling bitumen quality while the froth is being processed.

Canadian Patent Application No. 2,644,821 (Chakrabarty et al.) filed on Nov. 26, 2008, published on May 26, 2010, in the name of Imperial Oil Resources Limited, describes the use of a native bitumen marker for controlling the SB ratio of a process stream during solvent-assisted bitumen extraction. That application describes using one or more native bitumen markers (for example, sulfur, nickel, vanadium, iron, copper, manganese, or chromium) to measure the SB in a process stream, for instance a stream from a froth separation unit (FSU) and/or to measure hydrocarbon loss, for instance in a tailings solvent recovery unit (TSRU).

SUMMARY OF THE INVENTION

Described herein is a method of controlling bitumen quality in a hydrocarbon stream, for instance a hydrocarbon stream from a froth separation unit (FSU), within a solvent-assisted bitumen extraction operation. Bitumen quality refers to the amount of selected contaminants in the hydrocarbon stream. Contaminants may include asphaltenes (comprising metal porphyrins) and inorganic or mineral solids (comprising inorganic elements, e.g. Si, Al, Ti, Fe, Na, K, Mg, and Ca). In controlling the bitumen quality, the amount of each selected contaminant is first measured. Next, the measured value is compared to the maximum reference value for each contaminant. Where one or more of these contaminants is higher than the maximum reference value, at least one variable of the solvent-assisted bitumen extraction is adjusted to improve bitumen quality.

In a first aspect, the present invention provides a method of controlling asphaltene content or inorganic solids content in a hydrocarbon stream during a solvent-assisted bitumen extraction, comprising:

measuring (i) an amount of nickel or vanadium, or both, in the hydrocarbon stream as an indication of asphaltene content, and optionally estimating an asphaltene content based on the amount of nickel or vanadium, or both;

measuring (ii) an amount of inorganic elements in the hydrocarbon stream as an indication of inorganic solids content, and optionally estimating an amount of inorganic solids based on the amount of inorganic elements; and comparing the measured or estimated amounts of (i) and (ii) to maximum reference values, and, where the measured or estimated amounts of (i) or (ii) are higher than the maximum reference value, adjusting at least one variable of the solvent-assisted bitumen extraction to control the asphaltene content or the inorganic solids content in the hydrocarbon stream.

In certain embodiments, the following features may be present. The measuring of (i) and (ii) may be effected using X-Ray Fluorescence, inductively coupled plasma, atomic absorption, or electron spin resonance. The method may comprise estimating the asphaltene content based on the amount of nickel or vanadium, or both. The method may comprise estimating the inorganic solids content based on the amount of inorganic elements. The method may further comprise measuring (iii) an amount of sulfur in the hydrocarbon stream, and comparing the measured amount of (iii) to a maximum reference value, and adjusting at least one variable of the solvent-assisted bitumen extraction, if necessary, based on the measured amount as compared to the maximum reference value. The measuring of (iii) may be effected using X-Ray Fluorescence, inductively coupled plasma, atomic absorption, or electron spin resonance. The inorganic elements may comprise at least one of Si, Al, Ti, Ca, Fe, and Mg. The inorganic elements may comprise Si, Al, Ti, Ca, Fe, and Mg. The inorganic elements may further comprise Na or K. The solvent-assisted bitumen extraction may be an aqueous solvent extraction process. The hydrocarbon stream may be a hydrocarbon leg from a froth separation unit of the solvent-assisted bitumen extraction. The hydrocarbon stream may be a hydrocarbon leg from a solvent recovery unit of the solvent-assisted bitumen extraction. The solvent-assisted bitumen extraction may be a paraffinic froth treatment. The at least one variable may comprise a solvent to bitumen froth ratio. The at least one variable may comprise an amount of solvent. The at least one variable may comprises an amount of bitumen froth. The at least one variable may comprise bitumen froth quality. The at least one variable may comprise residence time in a separation vessel. The at least one variable may comprise temperature in a separation vessel. The at least one variable may comprise pressure in a separation vessel. The solvent-assisted bitumen extraction may be a non-aqueous solvent extraction process. The method may be operated continuously. The method may further comprise, periodically or before the measuring (ii), identifying minerals in the hydrocarbon stream. The indentifying may be effected by X-Ray Fluorescence or with a Scanning Electron Microscope and Energy Dispersive X-Ray. The method may further comprise;

measuring element concentrations in the hydrocarbon stream and converting the element concentration to mineral concentrations. The conversion may be effected by multiplying each element concentration by the ratio of molecular weight of a mineral to the atomic weight of an element of interest. The method may further comprise adding all mineral concentrations together to obtain the amount of inorganic solids. The method may further comprise using a calibration relationship between an actual amount of inorganic solids, obtained by taking offline samples, filtering solids out, and weighing dried filtered solids, and the measured amount of inorganic solids, to calibrate the measured amount of inorganic solids.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached figures, wherein.

DETAILED DESCRIPTION

"Solvent-assisted bitumen extraction" as used herein is a process used to extract bitumen from mined oil sands using solvent. The solvent may be, but is not limited to, a paraffinic (saturated aliphatic) solvent. The extraction process may be aqueous or non-aqueous.

"Hydrocarbon stream" as used herein means a stream stemming from mined oil sands, which comprises hydrocarbons, and which has been processed using a bitumen extracting solvent. The hydrocarbon stream may be, but is not limited to, a hydrocarbon leg following bitumen extraction using a paraffinic bitumen extracting solvent or a hydrocarbon leg following bitumen extraction using a non-aqueous bitumen extracting solvent.

"Bitumen quality" as used herein is an indicator of the amount of selected contaminants in the process stream. Of course, lower amounts of contaminants mean a higher bitumen quality. Contaminants may include, but are not limited to, asphaltenes (comprising metal porphyrins) and inorganic or mineral solids (comprising inorganic elements, e.g. Si, Al, Ti, Fe, Na, K, Mg, and Ca).

"Bitumen froth quality" as used herein means a composition of bitumen, water and solids in the feed bitumen-froth to a solvent extraction unit. A higher quality of bitumen-froth comprises higher concentrations of bitumen and lower concentrations of solids.

"Asphaltenes" as used herein are pentane insoluble, toluene soluble components of carbonaceous materials such as bitumen, crude oil, or coal. Generally, asphaltenes comprise carbon, hydrogen, nitrogen, oxygen, sulfur, vanadium and nickel. As mentioned earlier, a portion of the asphaltenes in bitumen is precipitated during bitumen-froth treatment using a paraffinic solvent.

A brief background of metal porphyrins will now be provided. Viscous hydrocarbons, for example bitumen, comprise relatively large quantities of metals, mainly vanadium and nickel, much of which is believed to be complexed in chemical structures called porphyrins. These metal porphyrins tend to be predominantly present in the asphaltenes, whose precipitation in the PFT process tends to lower their concentrations and those of Ni and V in the product bitumen.

Described herein is a method of controlling bitumen quality in a hydrocarbon stream within a solvent-assisted bitumen extraction operation, for instance a hydrocarbon stream from a froth separation unit (FSU). Bitumen quality refers to the amounts of selected contaminants in the process stream. Contaminants may include asphaltenes (comprising metal porphyrins) and inorganic solids (comprising inorganic elements, e.g. Si, Al, Ti, Fe, Na, K, Mg, and Ca). Contaminants may also include sulfur. First, the amounts of selected contaminants are measured. Next, these measured values are compared to maximum reference values. Where one or more of these contaminants is higher than the maximum reference value, at least one variable of the solvent-assisted bitumen extraction is adjusted to improve bitumen quality.

The contaminants may be measured indirectly by measuring their constituent elements and then using established correlations relating the contaminants with the constituent elements. The correlations between contaminants and the constituent elements may be established from laboratory or plant data.

Figure 4:
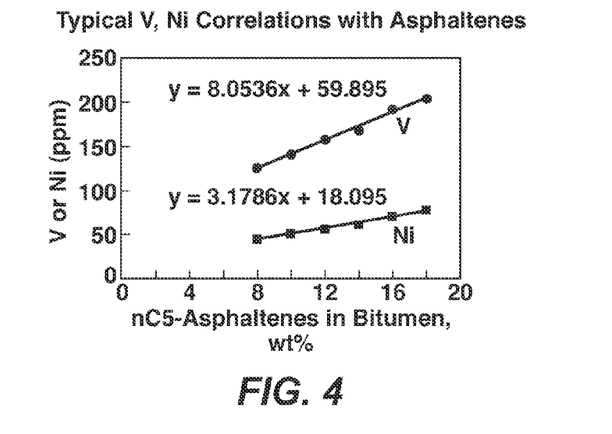
FIG. 4 is a non-limiting graph illustrating correlations between nickel content and asphaltene content in bitumen, and between vanadium content and asphaltene content in bitumen.
Figure 5:
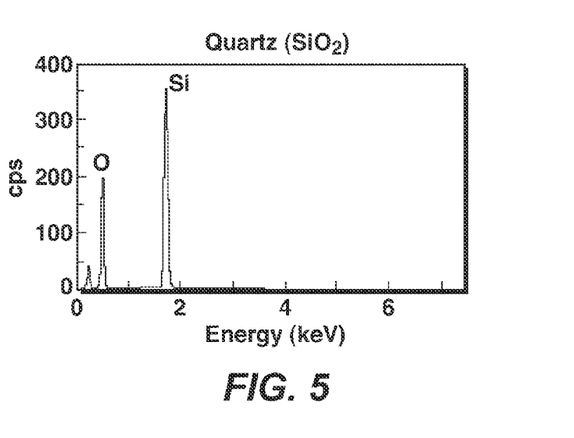
FIG. 5 is a graph identifying quartz ($SiO_2$) by a Scanning Electron Microscope and Energy Dispersive X-Ray (SEM-EDS) in PFT bitumen.
Figure 6:
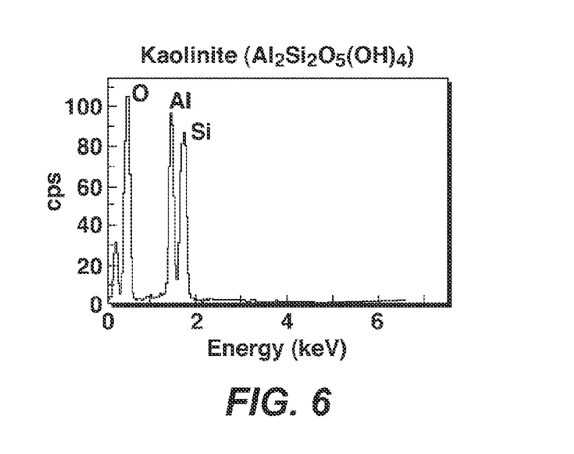
FIG. 6 is a graph identifying kaolinite ($Al_2Si_2O_5(OH)_4$) by SEM-EDS in PFT bitumen.
Figure 7:
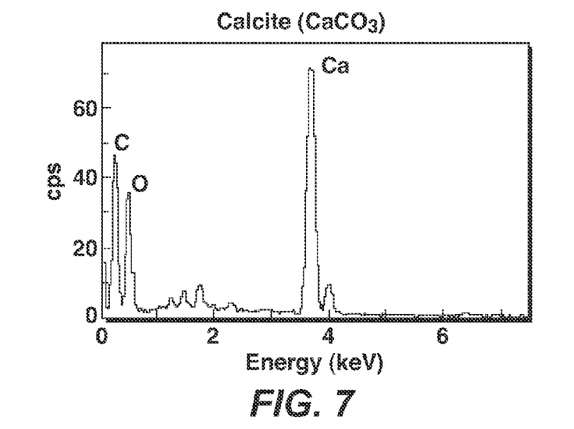
FIG. 7 is a graph identifying calcite ($C_aCO_3$) by an SEM-EDS in PFT bitumen.
Figure 8:
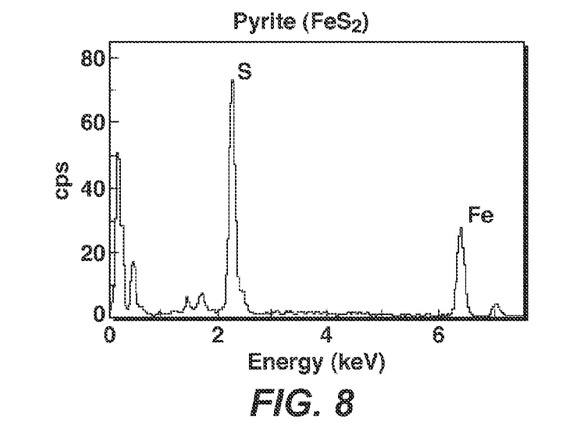
FIG. 8 is a graph identifying pyrite ($FeS_2$) by an SEM-EDS in PFT bitumen.
Figure 9:
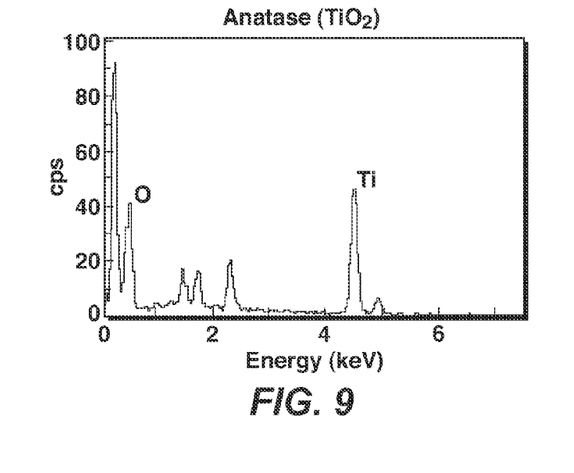
FIG. 9 is a graph identifying anatase ($TiO_2$) by an SEM-EDS in PFT bitumen.

The asphaltenes contaminant may be indirectly measured using the correlations between measured nickel and/or vanadium content in the hydrocarbon stream and asphaltene content. FIG. 4 is a non-limiting graph illustrating correlations between nickel content and asphaltene content in bitumen, and between vanadium content and asphaltene content in bitumen. From these correlations, maximum nickel and/or vanadium reference values could be selected which are representatives of a maximum asphaltene reference value so that adjustments to the process could be made based on the measured nickel and/or vanadium content, without necessarily measuring or estimating the asphaltene content.

The inorganic solids contaminant may be indirectly measured from the measured inorganic elements (Si, Al, Ti, Fe, Na, K, Mg, and Ca). The steps involved for doing this, according to one embodiment of this invention, are described below.

The sulfur contaminant may be directly measured.

One method to measure the asphaltenes and inorganic solids contaminants is by measuring vanadium, nickel and inorganic elements (Si, Al, Ti, Fe, Na, K, Mg, and Ca) by X-Ray Fluorescence (XRF). Other methods include, but are not limited to, Inductively Coupled Plasma (ICP), Atomic Absorption (AA), and Electron Spin Resonance (ESR). The above methods may also be used to measure the sulfur contaminant.

Figure 2:
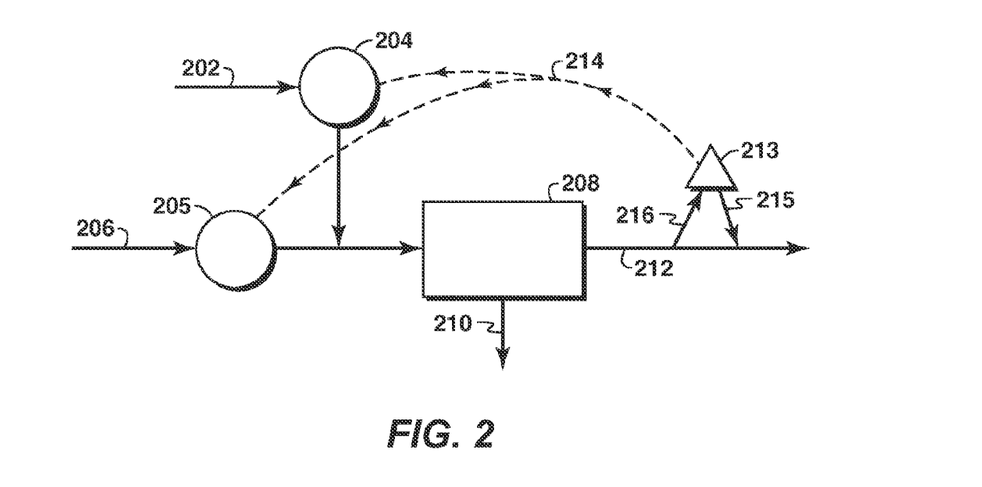
FIG. 2 is a schematic of a system for controlling bitumen quality according to a disclosed embodiment.

One way of practicing an embodiment of the present invention is illustrated in FIG. 2 in which a paraffinic solvent (202) (for example, pentane or hexane mixed with isomers of pentanes or hexanes) is metered and pumped through a metering pump (204) to the froth stream (206) metered through a metering pump (205). The froth and the solvent are well mixed in an on-line static mixer (not shown in FIG. 2) before it enters the FSU (208). For the sake of simplicity, only one FSU vessel is shown in FIG. 2.

In the FSU (208), the water along with asphaltenes and fines settle out at the bottom and are removed as the water leg (210) from the vessel. The diluted PFT bitumen (212) exits from the top of the vessel. An on-line X-Ray Fluorescence (XRF) unit (213) measures the amounts of selected contaminants in a portion of the hydrocarbon leg (216). A feedback control system compares these measured amounts with the maximum reference values of these contaminants. If the measured contaminant amount is higher than the maximum reference value, the control system sends a signal (214) to one or both of the metering pumps (204 and 205) to adjust the amount of solvent or froth, or both. The portion (215) of the hydrocarbon leg exiting the XRF unit (213) is also shown.

Various other adjustments to the solvent-assisted process could be made. Non-limiting examples include solvent to bitumen froth ratio, amount of solvent feed, amount of bitumen froth feed, residence time in the separation vessel, temperature in the separation vessel, pressure in the separation vessel, bitumen froth quality, or the addition of additives to accelerate the particle settling.

Figure 3:
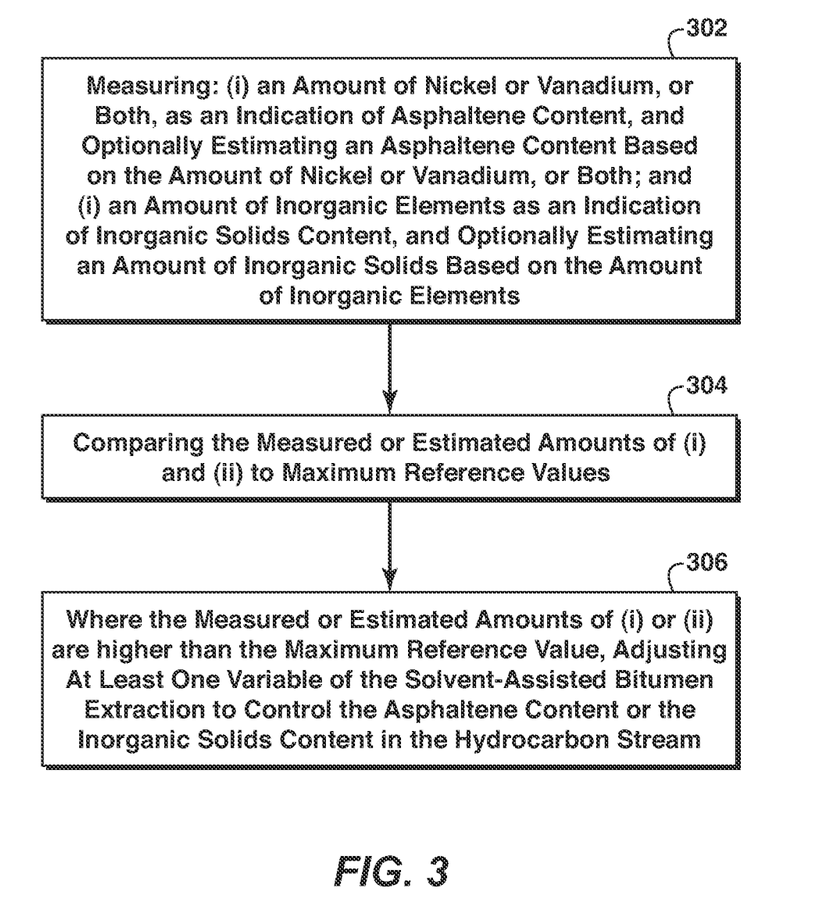
FIG. 3 is a flow diagram of a process for controlling bitumen quality according to a disclosed embodiment.

FIG. 3 is a flow chart of one embodiment. The method shown in FIG. 3 comprises the following steps:

measuring: (i) an amount of nickel or vanadium, or both, as an indication of asphaltene content, and optionally estimating an asphaltene content based on the amount of nickel or vanadium, or both; and (ii) an amount of inorganic elements as an indication of inorganic solids content, and optionally estimating an amount of inorganic solids based on the amount of inorganic elements (302);

comparing the measured or estimated amounts of (i) and (ii) to maximum reference values (304); and where the measured or estimated amounts of (i) or (ii) are higher than the maximum reference value, adjusting at least one variable of the solvent-assisted bitumen extraction to control the asphaltene content or the inorganic solids content in the hydrocarbon stream (306).

As described above, the measured amount of nickel or vanadium, or both, may be converted to asphaltenes content. The reason that this is optional is that, the method is purposed to control asphaltene content, and if a relationship between the amount of nickel, vanadium, or both and asphaltene content has already been established, the method may omit the step of actually estimating the asphaltene content and simply compare the measured amount of nickel, vanadium, or both, to the maximum reference value for nickel, vanadium, or both. If the measured value is converted to an estimated asphaltene value, this estimated value can be compared to the maximum asphaltene reference value. This equally applies to the optional step of estimating the inorganic solids content step.

As mentioned above, methods according to embodiments of the instant invention may be used with non-aqueous solvent extraction streams. By way of example only, the following references are mentioned, all of which relate to non-aqueous extraction: Sparks et al., Fuel 1992 (71); 1349-1353; Canadian Patent Application 2,068,895 of Sparks et al.; and U.S. Pat. No. 4,057,486 of Meadus et al.

In one embodiment, the following three steps may be performed to determine the solid content in the hydrocarbons stream.

Step 1: Identifying Minerals by X-Ray Diffraction (XRD) or SEM-EDS

The minerals in the solids are first identified using XRD or SEM-EDS. This is done offline occasionally to make sure the mineral types in the product have been correctly identified. Typical minerals identified in PFT bitumen are quartz ($SiO_2$), kaolinite ($Al_2Si_2O_5(OH)_4$), calcite ($CaCO_3$), pyrite ($FeS_2$) and titanium-bearing minerals such as anatase ($TiO_2$), as shown in the graphs of FIGS. 5 to 9, obtained by an SEM-EDS. The cps on the y-axis in these figures represents X-ray counts per second and keV on the x-axis stands for kiloelectron volt.

Step 2: Measuring Key Elements in Identified Minerals and Converting to Mineral Concentration.

Figure 10:
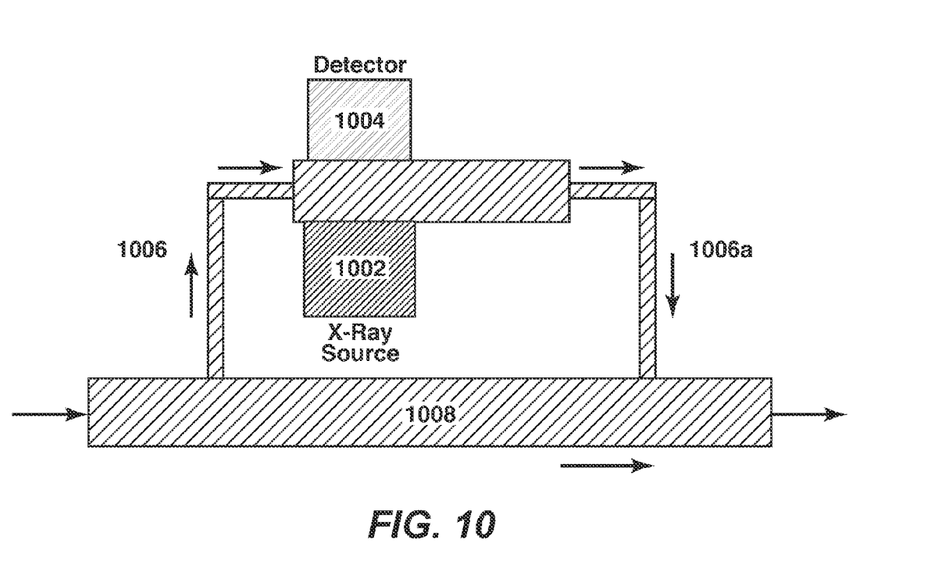
FIG. 10 is a schematic illustrating non-destructive continuous measurement of certain mineral elements in PFT bitumen in accordance with a disclosed embodiment.

As shown in FIG. 10, key elements (e.g., Si, Al, Fe, Ti, Ca) in the identified minerals are then measured on-line continuously using XRF (with an X-ray source (1002) and a detector (1004) on a slip stream (1006) taken from the main stream (1008) of the PFT bitumen. The analyzed slip stream (1006*a*) is re-combined with the main stream (1008). The key element concentrations are then converted to corresponding mineral concentrations by multiplying each elemental concentration by the ratio of the molecular weight of the mineral and the element of interest. Some elements (e.g., Si) originating from more than one minerals are distributed among their source minerals. All the mineral concentrations thus determined are added up to provide the total XRF-measured mineral concentrations.

The non-destructive, continuous measurement of the key elements allows real-time data collection without loss of any product stream.

Step 3: Converting XRF Mineral Concentrations to Total Solids Concentrations

To fine tune the solids quantification, a calibration graph relating the actual solids concentrations with the XRF-measured concentrations (from Step 2) is generated. The actual solids concentrations are determined offline by taking samples, filtering the solids out and weighing the dried filtered solids.

Any change in the mineral types in the bitumen product during operation of the plant is monitored from time to time through examination of the minerals using XRD or SEM-EDS. Any change is reflected in Steps 2 and 3.

In addition to measuring the solids on-line, the process may be controlled to achieve product with target solids level. This is accomplished by measuring the solids concentration on-line on a slip stream, and sending a signal to take corrective action through a feedback control loop.

The solids measurements and feedback loop can also be implemented in the product bitumen coming out of the SRU after the solvent has been recovered. This embodiment will allow measurements of elements, whose concentrations may be too low for detection and measurement in the diluted bitumen from the FSU, but high enough for detection and measurement in the SRU product bitumen.

EXAMPLES

Example 1

Using Inorganic Elements to Determine Solids Content

To determine the solids content from the measured inorganic elements, the following steps were used.

Step 1: Identifying Minerals by SEM-EDS or XRD

Five minerals were identified by SEM-EDS in the solids from the bitumen in a PFT pilot conducted by IOR at CAN-MET (Canada Centre for Mineral and Energy Technology). The names of the minerals, their formulas and molecular weights are shown in Table 1. The key elements in these minerals are Si, Al, Ca, Fe and Ti.

TABLE 1

Properties of Minerals Identified by SEM-EDS in PFT Bitumen Solids

| Minerals | Formula | MW |
|---|---|---|
| Quartz | SiO2 | 60.09 |
| Kaolinite | $Al_2Si_2O_5(OH)_4$ | 258.13 |
| Calcite | $CaCO_3$ | 100.09 |
| Pyrite | $FeS_2$ | 119.98 |
| Anatase | $TiO_2$ | 79.87 |

Step 2: Measuring Key Elements by XRF and Converting to Mineral Concentration

For the purpose of this illustration, it is assumed that an on-line XRF instrument has been used to measure the concentrations of the key elements, as shown in the second column of Table 2.

To determine the mineral concentrations of kaolinite ($Al_2Si_2O_5(OH)_4$, calcite ($CaCO_3$), pyrite ($FeS_2$) and anatase ($TiO_2$), the Al, Ca, Fe, and Ti concentrations were each multiplied by the ratio of the corresponding mineral MW to the key element's atomic weight (Column 4, Table 2).

To determine the mineral concentrations of quartz ($SiO_2$), the Si concentration of 5.20 ppm corresponding to the kaolinite was subtracted from the total 45 ppm of Si measured and then the remaining 39.80 ppm of Si (from quartz) was multiplied by the ratio of the MW of quartz to Si. This led to a quartz concentration of 85.14 ppm in the product bitumen.

The total minerals concentration was then added up to provide total solids of 178.14 ppm by XRF in the PFT product bitumen.

TABLE 2

Measured Elemental, Converted Minerals and Total Solids Concentration by XRF

| Elements | Measured Conc. ppm | Minerals Type | Calc. Minerals Conc. ppm | Total Solids by XRF ppm |
|---|---|---|---|---|
| | | | | 178.14 |
| Al | 5 | Al$_2$Si$_2$O$_5$(OH)$_4$ | 23.92 | |
| Ca | 10 | CaCO$_3$ | 24.97 | |
| Fe | 5 | FeS$_2$ | 10.74 | |
| Ti | 20 | TiO$_2$ | 33.37 | |
| Si (from Quartz and Kaolinite)* | 45 | Quartz | 85.14 | |
| *Si from Kaolinite | 5.20 | | | |
| *Si from Quartz | 39.80 | | | |

Figure 11:
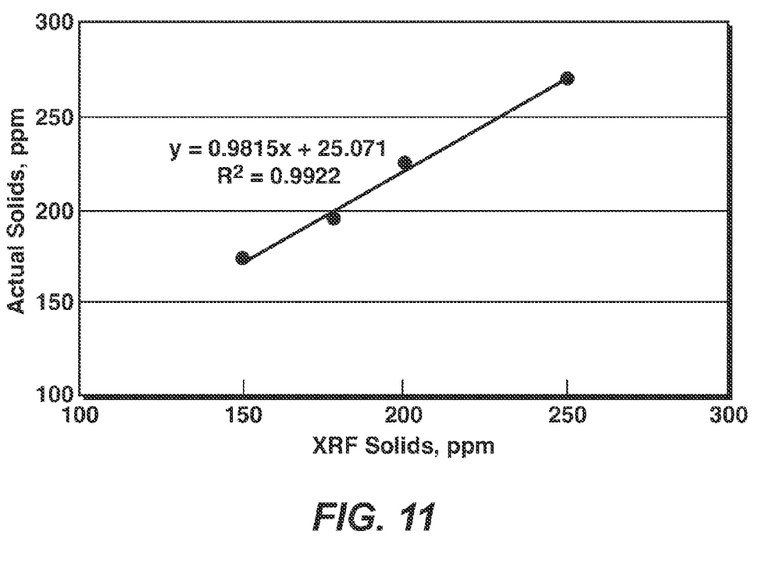
FIG. 11 is a calibration graph relating X-Ray Fluorescence (XRF) total solids concentration with actual total solids concentration.

Step 3: Converting XRF Solids to Actual Solids Concentration Through Calibration A calibration graph relating the actual solids to the XRF solids (Step 2) was generated by taking samples of the PFT product bitumen and determining the solids through filtration, drying and weighing. Some hypothetical data on solids by XRF and actual solids measured offline in the lab are shown below to illustrate the calibration. FIG. 11 shows a linear relationship for the hypothetical data.

This calibration graph can be used to convert XRF measured total solids concentration (Step 2) to the "actual" solids concentration.

TABLE 3

Solids Concentration by XRF and Actual Solids Concentration for Calibration

| Solids Conc. by XRF (ppm) | Actual Solids Conc. (ppm) |
|---|---|
| 178.14 | 195 |
| 200 | 225 |
| 250 | 270 |
| 150 | 174 |

Example 2

Using V or Ni to Determine Asphaltenes Content

To determine the asphaltenes content in the product bitumen, V and Ni were measured using atomic absorption (these could alternatively be determined using an on-line XRF). A calibration graph or equation relating V to asphaltenes content in the bitumen was prepared. The equation is: V (ppm) =59.9+8.05 (asphaltenes in bitumen, wt %). The asphaltene content can be determined using the above equation by measuring the V in the product bitumen and compared with the target asphaltene concentration range. By incorporating the equation in the computer program of the control algorithm, at least one process variable may be adjusted to achieve the target asphaltene level in the bitumen product.

A calibration graph or equation relating Ni to asphaltenes content in the bitumen was also prepared. The equation is: Ni (ppm)=18.1+3.18 (asphaltenes in bitumen, wt %). The asphaltene content can be determined using the above equation by measuring the Ni in the product bitumen and compared with the target asphaltene concentration range. By incorporating the equation in the computer program of the control algorithm, at least one process variable may be adjusted to achieve the target asphaltene level in the product bitumen.

In the preceding description, for purposes of explanation, numerous details are set forth in order to provide a thorough understanding of the embodiments of the invention. However, it will be apparent to one skilled in the art that these specific details are not required in order to practice the invention.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments of the invention are intended to be examples only. Alterations, modifications and variations can be effected to the particular embodiments by those of skill in the art without departing from the scope of the invention, which is defined solely by the claims appended hereto.

What is claimed is:

1. A method of controlling asphaltene content, inorganic solids content, and sulfur content in a hydrocarbon stream during a solvent-assisted bitumen extraction, comprising:
    measuring (i) an amount of nickel or vanadium, or both, in the hydrocarbon stream as an indication of asphaltene content, and optionally estimating an asphaltene content based on the amount of nickel or vanadium, or both;
    measuring (ii) an amount of at least one of Si, Al, Ti, Ca, Fe, Na, K, and Mg in the hydrocarbon stream as an indication of inorganic solids content, and optionally estimating an amount of inorganic solids based on the amount of the at least one of Si, Al, Ti, Ca, Fe, Na, K, and Mg;
    measuring (iii) an amount of sulfur in the hydrocarbon stream; and
    comparing the measured or estimated amounts of (i), (ii), and (iii) to maximum reference values, and, where the measured or estimated amounts of (i), (ii), or (iii) are higher than the maximum reference value, adjusting at least one variable of the solvent-assisted bitumen extraction to control the asphaltene content, the inorganic solids content, or the sulfur content in the hydrocarbon stream;
    wherein the solvent-assisted bitumen extraction is a paraffinic froth treatment, and
    wherein the hydrocarbon stream is a hydrocarbon leg from a froth separation unit of the solvent-assisted bitumen extraction, or is a hydrocarbon leg from a solvent recovery unit of the solvent-assisted bitumen extraction.

2. The method of claim 1, wherein the measuring of (i), (ii) and (iii) is effected using X-Ray Fluorescence.

3. The method of claim 1, wherein the measuring of (i), (ii) and (iii) is effected using inductively coupled plasma, atomic absorption, or electron spin resonance.

4. The method of claim 1, further comprising estimating the asphaltene content based on the amount of nickel or vanadium, or both.

5. The method of claim 1, further comprising estimating the inorganic solids content based on the amount of the at least one of Si, Al, Ti, Ca, Fe, Na, K, and Mg.

6. The method of claim 1, wherein the at least one variable comprises a solvent to bitumen froth ratio.

7. The method of claim 1, wherein the at least one variable comprises an amount of solvent.

8. The method of claim 1, wherein the at least one variable comprises an amount of bitumen froth.

9. The method of claim 1, wherein the at least one variable comprises bitumen froth quality.

10. The method of claim 1, wherein the at least one variable comprises residence time in a separation vessel.

11. The method of claim 1, wherein the at least one variable comprises temperature in a separation vessel.

12. The method of claim 1, wherein the at least one variable comprises pressure in a separation vessel.

13. The method of claim 1, wherein the method is operated continuously.

14. The method of claim 1, further comprising, periodically or before the measuring (ii), identifying minerals in the hydrocarbon stream.

15. The method of claim 14, wherein the identifying is effected by X-Ray Fluorescence or with a Scanning Electron Microscope and Energy Dispersive X-Ray.

16. The method of claim 14, further comprising measuring element concentrations in the hydrocarbon stream and converting the element concentrations to mineral concentrations.

17. The method of claim 16, wherein the conversion is effected by multiplying each of the element concentrations by the ratio of molecular weight of a mineral to the atomic weight of an element of interest.

18. The method of claim 16, further comprising adding all mineral concentrations together to obtain the amount of inorganic solids.

19. The method of claim 1, further comprising using a calibration relationship between an actual amount of inorganic solids, obtained by taking offline samples, filtering solids out, and weighing dried filtered solids, and the measured amount of inorganic solids, to calibrate the measured amount of inorganic solids.

* * * * *